United States Patent [19]

Holroyd

[11] Patent Number: 5,016,480

[45] Date of Patent: May 21, 1991

[54] STRESS WAVE LOAD CELL

[75] Inventor: Trevor J. Holroyd, Derby, England

[73] Assignee: Stresswave Technology Limited, Derby, England

[21] Appl. No.: 480,836

[22] Filed: Feb. 16, 1990

[30] Foreign Application Priority Data

Mar. 14, 1989 [GB] United Kingdom ............... 8905822

[51] Int. Cl.$^5$ ............................................. G01L 1/00
[52] U.S. Cl. .................................. 73/862.59; 73/599
[58] Field of Search ............... 73/862.59, 702, 703, 73/599, DIG. 1, DIG. 4, 862.38

[56] References Cited

U.S. PATENT DOCUMENTS

| | | | |
|---|---|---|---|
| 3,153,338 | 10/1964 | Kleesattel | 73/862.59 X |
| 3,967,497 | 7/1976 | Brown | 73/DIG. 1 |
| 3,977,242 | 8/1976 | Brown | 73/862.59 |
| 4,604,612 | 8/1986 | Watkins et al. | 73/599 X |
| 4,679,430 | 7/1987 | Scott-Kestin et al. | 73/599 X |
| 4,712,037 | 12/1987 | Verbeek et al. | 73/702 X |

FOREIGN PATENT DOCUMENTS

| | | | |
|---|---|---|---|
| 0513276 | 5/1976 | U.S.S.R. | 73/DIG. 4 |
| 1430767 | 10/1988 | U.S.S.R. | 73/862.59 |

Primary Examiner—Charles A. Ruehl
Attorney, Agent, or Firm—Cushman, Darby & Cushman

[57] ABSTRACT

A stress wave load cell comprises a propagation member to which is acoustically coupled a transducer. Electrical pulses are supplied to the transducer from a pulse generator and the electrical pulses are converted into stress wave signals which propagate through the propagation member. The transducer also detects the stress waves after propagation through the propagation member and supplies an electrical signal to processor which gives a measure of the load applied to the load cell.

Damping members which have profiled surfaces are caused to move into damping contact with the propagation members when a load is applied to the load cell. The damping members damp the propagation of the stress waves in the propagation member and the damping is proportional to the area of damping contact, the area of damping contact increases with the load applied. May be used to measure tensile load or compressive load and may be used as a touch sensitive panel.

13 Claims, 2 Drawing Sheets

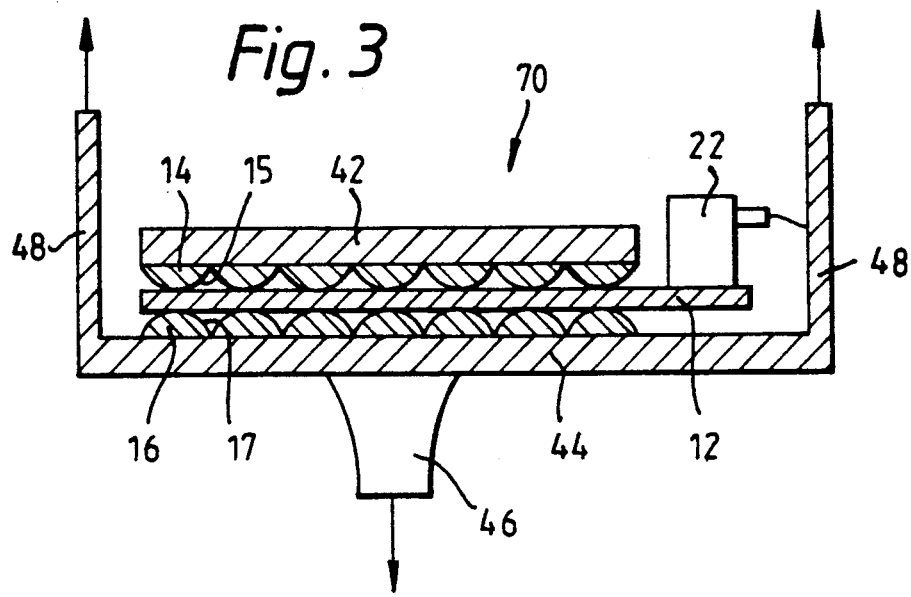
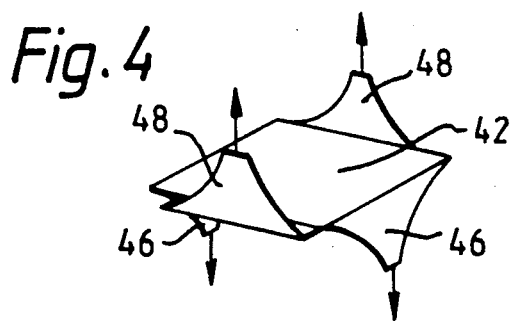
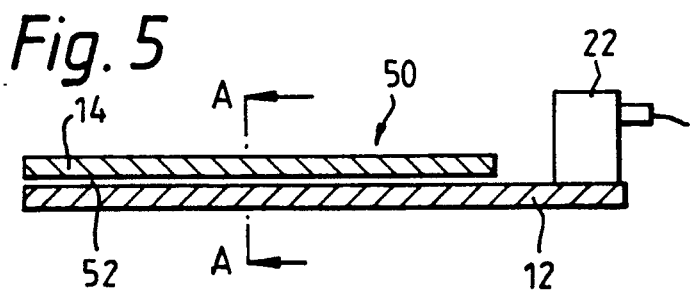
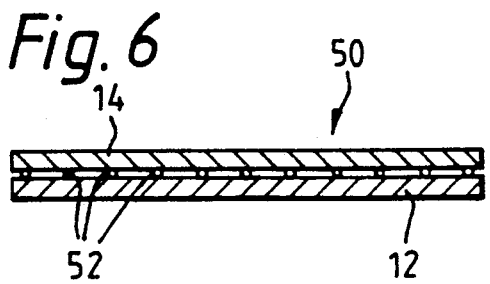

STRESS WAVE LOAD CELL

The present invention relates to load cells and in particular to a load cell which uses structure borne stress waves.

The present invention seeks to provide a novel stress wave load cell.

Accordingly the present invention provides a stress wave load cell comprising a propagation member which allows the propagation of stress waves therethrough, at least one transducer acoustically coupled to the propagation member, at least one damping member having a variable area of damping contact with at least one surface of the propagation member such that when a load is applied to the load cell the area of damping contact between the propagation member and the damping member increases with the load, the damping member is resilient such that the area of damping contact between the damping member and the propagation member is variable in a repeatable manner when a load is applied to the load cell, the at least one transducer being arranged to launch a stress wave signal into the propagation member and at least one means to detect the stress wave signal after it has propagated through the propagation member and been damped by any damping contact between the damping member and the propagation member, the at least one means to detect the stress wave signal being arranged to convert any detected stress waves into an electrical signal, a processor being arranged to process the electrical signal to give an electrical output signal as a measure of the load applied on the load cell.

The damping member may be deformable and have a deformable profiled surface which makes contact with the propagation member.

The deformable profiled surface may be substantially a corrugated shape.

The damping member may be formed from rubber.

A single transducer may launch the stress wave signal into the propagation member and the transducer is the at least one means to detect the stress wave signal after it has propagated through the propagation member.

A first transducer may launch the stress wave signal into the propagation member and a second transducer is the at least one means to detect the stress wave signal after propagation through the propagation member.

The load cell may measure compressive loads.

The load cell may measure tensile loads.

The propagation member may be a sheet, a first damping member may be arranged to move into damping contact with a first surface of the sheet and a second damping member may be arranged to move into damping contact with a second surface of the sheet, the first and second surfaces being substantially parallel.

Load transmission members may act on the first and second damping members to move them into contact with the propagation member, a biasing means may urge the load transmission members together or apart.

The damping member may be spaced from the propagation member by spacer means.

The spacer means may comprise a relatively loosely woven fabric.

The spacer means may comprise a gas layer.

The present invention will be more fully described by way of example with reference to the accompanying drawings, in which:

FIG. 3 is a cross-sectional view of a third embodiment of a stress wave load cell according to the present invention.

FIG. 4 is a perspective view of the stress wave load cell in FIG. 3.

FIG. 5 is a further embodiment of a stress wave load cell according to the present invention.

FIG. 6 is a cross-sectional view in the direction of arrows A in FIG. 5.

Figure 1:
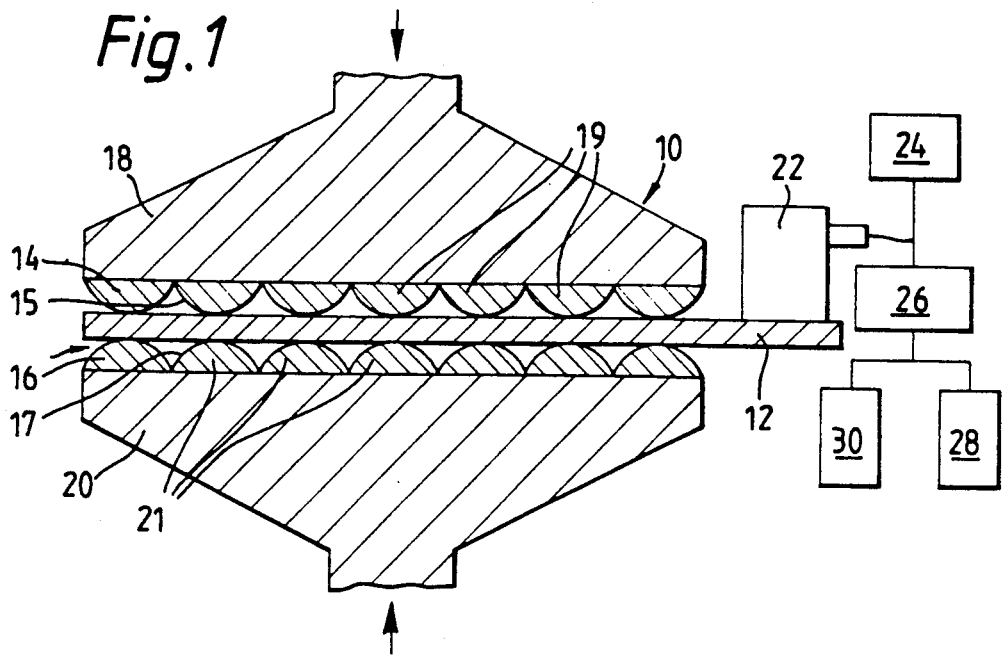
FIG. 1 is a cross-sectional view of a stress wave load cell according to the present invention.

A stress wave load cell 10 according to the present invention is shown in FIG. 1. The stress wave load cell 10 comprises a propagation member 12, which may be a sheet or bar, formed from a material which allows the propagation of stress waves therethrough. A first deformable damping member 14 and a second deformable damping member 16 are arranged in close proximity to opposite surfaces of the propagation member, 12. The surfaces 15 and 17 of the first and second damping members 14 and 16 respectively which confront the opposite surfaces of the propagation member 12 are profiled. In this example the surfaces 15 and 17 have a generally corrugated shape which in cross-section comprises a series of semi-circular areas 19 and 21. The damping members 14 and 16 are resilient and may be formed from rubber. A first load transmission member 18 and a second load transmission member 20 are arranged to act on the first and second deformable damping members 14 and 16 such that the deformable damping members 14 and 16 move into damping contact, or increase the area of damping contact, with the surfaces of the propagation member 12 when a load is applied to the load cell 10. An acoustic emission transducer 22 is acoustically coupled to the propagation member 12. The transducer 22 is electrically connected to a pulse generator 24 and to a signal processor 26. The signal processor 26 is electrically connected to a recorder 28 and a display 30. The signal processor 26 may be connected to only one of the recorder 28 or display 30 if desired.

In operation of the stress wave load cell 10 the application of a compressive load onto the load transmission members 18 and 20 causes the profiled surfaces 15 and 17 of the first and second deformable damping members 14 and 16 respectively to move into damping contact with the opposite surfaces of the propagation member 12. As the load applied to the load cell increases, the deformable damping members deform such that the area of damping contact between the corrugated surfaces 15 and 17 of the damping members 14 and 16 and the propagation member 12 increases, by deformation of the corrugations. The pulse generator 24 sends electrical pulses to the transducer 22, which converts the electrical pulses into stress wave pulses which are launched into the propagation member 12. The transducer 22 also detects the stress waves after they have propagated through the propagation member 12 and converts the stress wave pulses into electrical signals. The electrical signals corresponding to the stress wave pulses are processed by processor 26 to give an electrical output signal as a measure of the load applied on the load cell 10.

The rate of decay of a stress wave pulse launched into the propagation member 10 varies in relation to the area of damping contact between the corrugated surfaces 15 and 17 of the deformable damping members 14 and 16 and the propagation member 12. Thus increasing the load on the load cell 10 increases the area of damping contact between the deformable damping members 14 and 16 and the propagation member 12, which causes greater damping of the stress waves propagating through the propagation member 12 and results in a reduction in the magnitude or level of the stress waves detected by the transducer 22.

The use of the profiled surfaces 15 and 17 on the deformable damping members 14 and 16 allows the area of damping contact between the propagation member 12 and the deformable damping members 14 and 16 to be varied in a controlled and repeatable manner, when a load is applied to the load cell. The particular profile of the surfaces 15 and 17 of the damping members 14 and 16 may be tailored to the specific application in order to alter the rate of change of damping as a function of the applied load. The total area of the deformable damping members and the damping properties of the deformable damping member may also be changed for a specific application to alter the rate of change of damping as a function of the applied load.

The profiled surfaces may also comprise a corrugated shape which is sinusoidal in cross-section or a corrugated shape which in cross-section comprises a series of triangular areas. Other profiled surfaces may be used for example a plurality of hemispherical, part spherical or other types of projection.

Although the figure has shown the output of the signal processor 26 connected to a recorder 28 and display 30 it may be possible to use the electrical output signal as a feedback signal.

Figure 2:
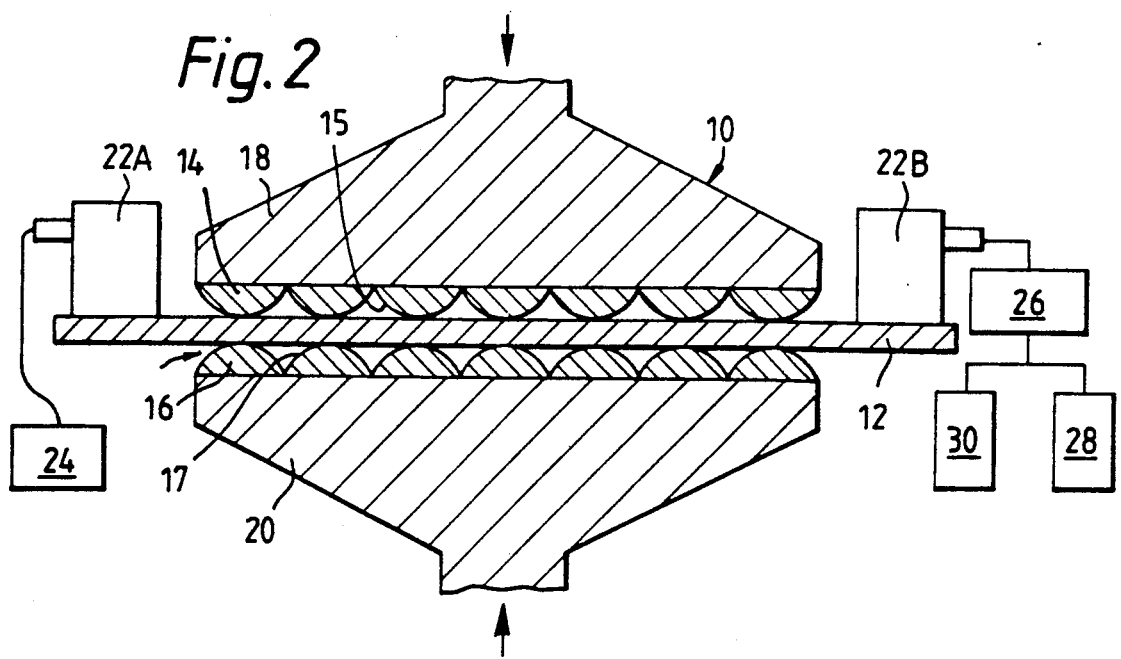
FIG. 2 is a cross-sectional view of a second embodiment of a stress wave load cell according to the present invention.

The stress wave load cell 10 in FIG. 2 is substantially the same as, and operates in the same manner as, the stress wave load cell in FIG. 1, but differs in that a first transducer 22A is electrically connected to the pulse generator 24 to launch the stress wave pulses into the propagation member 12, and a second transducer 22B, which detects stress wave pulses propagating through the propagation member 12, is electrically connected to the processor 26.

FIGS. 3 and 4 show a stress wave load cell 40 which is substantially the same as, and which operates in the same manner as the stress wave load cell 10 in FIG. 1, but differs in that the stress wave load cell 40 is arranged to measure tensile loads and the load transmission members 42 and 44 are provided with connecting members 46, 48 which extend towards the other load transmission member. The ends of the connecting members 46, 48 have the tensile load applied to them, and the load transmission members 42 and 44 cause the damping members 14 and 16 to apply a compressive load onto the propagation member 12.

A stress wave load cell 50 is shown in FIGS. 5 and 6 which is substantially the same as, and which operates in a similar manner to, the stress wave load cell 10 in FIG. 1. The stress wave load cell 50 is suitable for use as a load cell which may provide a sensitive response to a load acting in only a local area of a large surface. In such cases it is necessary to minimise the area of damping contact in the undisturbed or no load condition. To achieve this objective spacers 52 are provided between the damping member 14 and the propagation member 12, the spacers 52 prevent the damping member 14 from contacting or substantially contacting the propagation member 12 until a load is applied. The spacers 52 are chosen to be of relatively small dimension and have physical properties such that they do not give any significant amount of damping (e.g. due to an impedance mismatch). The spacers 52 may be attached to the damping member 14 or to the propagation member 12. The spacers 52 may comprise a number of point or line projections for example fibres or a loosely woven fabric. The spacer 52 may be a gas, i.e. air, film. When a load is applied between the damping member 14 and the propagation member 12 the spacers 52 may either yield, embed or retract into the damping member 14 to allow a substantial area of the damping member 14 to make damping contact with the propagation member 12. The stress wave load cell 50 would be suitable for use as a touch sensitive panel, for example as a safety buffer on an automatically guided vehicle. The stress wave load cell 50 would have even sensitivity over its area, and the use of a rubber damping member would enable a durable shaped touch sensitive panel highly resistant to damage to be produced.

It is to be noted that stress waves are waves which propagate in a structure as an elastic wave, and these elastic waves may consist of compressional waves, shear waves or other types of waves. These stress waves may be produced by any type of source process.

Although any suitable frequency may be used, it is normal practice to use frequencies above 20 KHz in order to reduce or minimise unwanted effects of external background sounds or noises.

It may be possible to profile the surfaces of the propagation member and to use a substantially planar damping members which flex under an applied load to contact a greater area of the propagation member.

I claim:

1. stress wave load cell comprising a propagation member which allows the propagation of stress waves therethrough, the propagation member having at least one surface, at least one damping member arranged such that when a load is applied to the load cell a damping load is applied on the at least one surface of the propagation member by the damping member, the damping load applied by the damping member increasing with the load, the at least one damping member having a variable area of damping contact with the at least one surface of the propagation member such that when a load is applied to the load cell the area of damping contact between the propagation member and the at least one surface of the damping member increases with the load, the at least one damping member being resilient such that the area of damping contact between the damping member and the at least one surface of the propagation member is variable in a repeatable manner when a load is applied to the load cell, at least one transducer acoustically coupled to the propagation member, the at least one transducer being arranged to launch a stress wave signal into the propagation member, at least one means acoustically coupled to the propagation member to detect the stress wave signal after it has propagated through the propagation member and been damped by any damping contact between the damping member and the propagation member, the at least one means to detect the stress wave signal being arranged to convert any detected stress waves into an electrical signal, a processor being arranged to process the electrical signal to give an electrical output signal as a measure of the load applied on the load cell.

2. A stress wave load cell as claimed in claim 1 in which the at least one damping member is deformable and has a deformable profiled surface which makes contact with the propagation member.

3. A stress wave load cell as claimed in claim 2 in which the deformable profiled surface is substantially a corrugated shape.

4. A stress wave load cell as claimed in claim 2 in which the at least one damping member is formed from rubber.

5. A stress wave load cell as claimed in claim 1 in which a single transducer launches the stress wave signal into the propagation member and the transducer is the at least one means to detect the stress wave signal after it has propagated through the propagation member.

6. A stress wave load cell as claimed in claim 1 in which a first transducer launches the stress wave signal into the propagation member and a second transducer is the at least one means to detect the stress wave signal after propagation through the propagation member.

7. A stress wave load cell as claimed in claim 1 in which the load cell measures compressive loads.

8. A stress wave load cell as claimed in claim 1 in which the load cell measures tensile loads.

9. A stress wave load cell as claimed in claim 1 in which the propagation member is a sheet, a first damping member is arranged to have variable damping contact with a first surface of the sheet and a second damping member is arranged to have variable damping contact with a second surface of the sheet, the first and second surfaces being substantially parallel.

10. A stress wave load cell as claimed in claim 9 in which load transmission members act on the first and second damping members to move them into contact with the propagation member, a biasing means urging the load transmission members together or apart.

11. A stress wave load cell as claimed in claim 1 in which the damping member is spaced from the propagation member by spacer means.

12. A stress wave load cell as claimed in claim 11 in which the spacer means comprises a relatively loosely woven fabric.

13. A stress wave load cell as claimed in claim 11 in which the spacer means comprises a gas layer.

* * * * *